United States Patent [19]
Diels et al.

[11] Patent Number: 6,013,511
[45] Date of Patent: *Jan. 11, 2000

[54] PRECIPITATING METALS OR DEGRADING XENOBIOTIC ORGANIC COMPOUNDS WITH MEMBRANE IMMOBILIZED MICROORGANISMS

[75] Inventors: Ludo Diels, Oelegem; Roger Leysen, Mol; Sandra Van Roy, Lil; Willy Doyen, Wommelgen; Maximilien Mergeay, Retie, all of Belgium

[73] Assignee: Vito, Belgium

[ * ] Notice: This patent issued on a continued prosecution application filed under 37 CFR 1.53(d), and is subject to the twenty year patent term provisions of 35 U.S.C. 154(a)(2).

[21] Appl. No.: 08/667,435

[22] Filed: Jun. 21, 1996

Related U.S. Application Data

[63] Continuation-in-part of application No. 08/133,118, Nov. 5, 1993, abandoned.

[51] Int. Cl.$^7$ ............... B09B 3/00; C12N 11/08; C12M 1/00; C02F 3/00

[52] U.S. Cl. .......... 435/262.5; 210/601; 210/611; 435/41; 435/177; 435/180; 435/289.1; 435/297.1

[58] Field of Search ............... 435/41, 174, 176, 435/177, 180, 182, 288, 262.5, 289.1, 297.1; 210/601, 611, 644, 685

[56] References Cited

U.S. PATENT DOCUMENTS

| | | | |
|---|---|---|---|
| 3,883,393 | 5/1975 | Knazek et al. | 435/400 |
| 4,440,853 | 4/1984 | Michaels et al. | 435/68 |
| 4,921,612 | 5/1990 | Surkar | 210/644 |
| 4,963,494 | 10/1990 | Hibino et al. | 435/288 |
| 4,988,443 | 1/1991 | Michaels et al. | 210/611 |
| 5,055,402 | 10/1991 | Greene et al. | 435/174 |
| 5,279,745 | 1/1994 | Jeffers et al. | 210/688 |

FOREIGN PATENT DOCUMENTS

| | | |
|---|---|---|
| 0241995 | of 0000 | European Pat. Off. . |
| 2 238 276 | 9/1987 | European Pat. Off. . |
| 0 355 910 | 2/1990 | European Pat. Off. . |
| 63-188386 | 8/1988 | Japan . |
| 2 178 447 | 2/1987 | United Kingdom . |

OTHER PUBLICATIONS

Inloes et al., "Hollow–Fiber Membrane Bioreactors Using Immobilized *E. coli* for Protein Synthesis", *Biotechnology and Bioengineering*, 25, 2653–2681 (1983).

*Primary Examiner*—David M. Naff
*Attorney, Agent, or Firm*—Merchant & Gould P.C.

[57] ABSTRACT

Precipitating of metals and degrading of xenobiotic organic compounds is carried out with a reactor containing microorganisms immobilized on a membrane made of an inorganic oxide such as $ZrO_2$, $Sb_2O_3$, or $Al_2O_3$ and an organic polymer such as polysulfone. The membrane has a skin side and an open side, and pores of the skin side are smaller than pores of the open side. The microorganisms are immobilized as a biofilm on the skin side of the membrane. A nutrient chamber supplies a nutrient solution to the open side of the membrane and the nutrient solution passes through the membrane from the open side to contact the microorganisms on the skin side. An effluent chamber supplies an effluent solution containing a metal in the form of a salt, a xenobiotic compound such as a chlorinated organic compound or both to the biofilm of microorganisms on the skin side, and the microorganisms precipitate the metal and/or degrade the xenobiotic compound. The concentration of nutrients in the nutrient chamber is kept sufficiently low so that the microorganisms of the biofilm utilize essentially all nutrients that pass through the membrane to prevent essentially any nutrients from entering the effluent solution. The membrane separates the effluent chamber and nutrient chamber such that leakage between the chambers is prevented.

27 Claims, 5 Drawing Sheets

PRECIPITATING METALS OR DEGRADING XENOBIOTIC ORGANIC COMPOUNDS WITH MEMBRANE IMMOBILIZED MICROORGANISMS

REFERENCE TO RELATED APPLICATIONS

This application is a continuation-in-part of application Ser. No. 08/133,118 filed Nov. 5, 1993, now abandoned, which application is incorporated herein by reference. This application and the parent application claim priority from European Patent Application 91400986.5 filed Apr. 12, 1991, which application is incorporated herein by reference.

BACKGROUND OF THE INVENTION

1. Field of the Invention

The invention relates to membranes with immobilized microorganisms thereon and/or therein, to biofilm obtainable with such membranes, to a process for obtaining such membranes, and to reactors including said membranes and to a process involving the use of said membranes, in particular for the elimination of metals or of xenobiotic organic compounds.

2. Description of the Prior Art

Soluble metal removal is a technical challenge which must be met before the recycling process water or avoiding toxic discharges in plant effluent.

Heavy metals such as cadmium, lead, copper and zinc draw the attention of the hygienists because of their toxicity. The public health is directly concerned with the occurrence of heavy metals in water and soil even at low concentrations owing to their accumulation in vegetables through soil solution or contact with the contaminated soil, or with water that has leached the contaminated soil. In the same way, sewage sludges produced in biological waste treatment can be also loaded with heavy metals and with the presence of toxic and recalcitrant organic compounds (pesticides, PCB's, chlorinated aromatics, and the like). Sewage sludges are often used as fertilizers. Furthermore, there is a tendency towards water reuse and rivers as reservoirs for drinking water. It is the reason why national and international authorities have issued directives on limit value for heavy metals in industrial effluents as well as in aquatic systems.

So, it appears desirable that these health hazards should be avoided. For this purpose, the best way should be the removal of heavy metals at the emission point i.e. from the industrial effluents.

The removal of heavy metals from industrial wastewaters can be performed by several strategies. Among them, chemical precipitation by addition of hydroxides or calcium oxides, ion-exchange on resin or electrolyses are of common practices. These methods are used when rather large amounts of metals, i.e. more than 500 ppm, are involved. However, they are not appropriate to remove intermediate amounts of metals or to degrade xenobiotic organic compounds.

The use of ion exchange is more interesting at very low concentrations (less than about 5 ppm). But each of these methods has disadvantages. One disadvantage of ion exchange is high resin costs. One disadvantage of electrolyses is high energy costs. One disadvantage of hydroxides or calcium oxides is high sludge production.

It has also been investigated to use biomass which is immobilized in porous polysulfone beads for extracting toxic and heavy metals from dilute waste streams. The beads were fabricated from high-density polysulfone dissolved in dimethylformamide (DMF). Dried, thermally-killed biomass produced by algae, yeast, bacteria, and aquatic flora were blended into the polysulfone-DMF solution, and spherical beads were formed by injecting the mixture into water.

Contaminants removed from the waters using these beads included arsenic, cadmium, copper, mercury, lead, manganese, and zinc. Laboratory tests indicated that the beads may be especially useful in treating dilute wastewaters containing metal concentrations up to about 15 mg/l (cf. Jeffers T. H. et al., 1989, "Biosorption of metal contaminants using immobilized biomass", Biohydrometallurgy p. 317–327). This is a method applicable for very low concentrations of metal ions.

In this case, it is necessary to regenerate the bacteria, because there is adsorption of the metals to be removed, on the sites of the bacteria, and very little precipitation, and then the sites of the bacteria become saturated. When the bacteria have been regenerated, their efficiency to adsorb metal is lowered because all the sites cannot be regenerated or some sites are destroyed. No high upconcentration can be obtained.

Furthermore, it is necessary to use a large amount of beads, because it is possible to adsorb only between 5 and 10% of the metal with respect to the biomass, whereas if precipitation could take place with such beads (which is not the case), it would be possible to eliminate at least about 50% of metal with respect to the biomass.

Debus O. et al. ("Aerobic mineralization of benzene, toluene and xylenes by microorganisms attached to gas-permeable membranes", Technical University of Hamburg-Harburg, FRG, April 1990) have disclosed the use of pure or mixed cultures of microorganisms to biodegrade volatile organics like benzene, toluene, ethylbenzene and the isomeric xylenes (BTEX), under aerobic conditions. In order to avoid the conventional aeration systems producing a large number of bubbles, leading to a BTEX loss by stripping, gas permeable membranes are used, such as silicon rubber. The loss of volatile organics can be minimized by allowing BTEX-mineralizing microorganisms to colonize the membrane surface and form a barrier to the escaping substances.

In the Debus method, the bacteria receive only oxygen from the membranes. Moreover, the bacteria form a biofilm on the membranes, because the pores are too small for the bacteria to be immobilized on or in the membrane, and the nutrients are in the effluents, which involves a contamination of the effluents.

It is known that some microorganisms can immobilize metals up to high concentrations in their cellular materials specially when they are attached on a support. Among the culture devices which promote the growth of microorganisms on a surface, the biological fluidized bed is attractive because it has excellent adhesion potentialities for bacteria. The biological fluidized bed is composed of a cylinder packed with inert particles such as sand, anthracite, glass beads, plastic, stone gravels which provide support for microbial growth. The particles are freely suspended in the nutritive solution by an upward flow (cf. Remacle J. et al., Heidelberg 1983, "Uptake of heavy metals from industrial effluents by microorganisms developed in a biological fluidised bed" p. 936–939).

One of the drawbacks of existing biological fluidized beds is the fact that the nutritive medium for the microorganisms is mixed with the effluent to be treated, which involves a contamination of the effluent. Moreover, important amounts of carbon are needed, because they are added into the effluent. In addition, there is a big release of the microorganisms. Both these factors increase the cost of the treatment of the effluent.

Reticulated polyurethane foams are interesting supports allowing a high retention and an easy recovery of biomass just by squeezing (Cooper P. F. et al., 1986, in Process Engineering Aspect of Immobilised Cell Systems p. 205–217 Webb C. et al. (eds), I. Chem. Eng.). These are essential characteristics for the development of a process of metal recovery from industrial effluents.

In reticulated foams, the immobilized cell cultures were conducted in fixed bed microfermenters (V=0.41) continuously fed with a nutrient medium. The support particles consisted in 3.4 cm cubes with an internal porosity of 98% and a pore aperture of 30 ppi (Colombi Y. et al., 1987, "Cadmium uptake by *Alcaligenes eutrophus* immobilized in reticulated polyurethane foam", Proc. 4th European Congress on Biotechnology, 1: 120).

Reticulated foams have their disadvantages as well. For example, the biofilm is on the surface of the pores, which implies that there is a big release of cells. Besides, there is a need for important amounts of carbon.

During the last years, bacteria resistant to a variety of heavy metals were isolated and identified (Silver S. et al., 1988, "Plasmid-mediated heavy metal resistances" Ann. Rev. Microbiol. 42, 717–743). The mechanisms for such resistance are often controlled by plasmid borne genes or by transposons. A remarkable example of those resistant bacteria is *Alcaligenes eutrophus* var. *metallotolerans*. The representative strain CH34 was isolated in sediments from a decantation basin of a zinc factory (Mergeay M. et al., 1978, "Extrachromosomal inheritance controlling resistance to cadmium, cobalt and zinc ions: evidence from curing in a Pseudomonas" Arch. Int. Physiol. Biochim. 86, 440–441). Strain CH34 bears two large plasmids (Mergeay M. et al., 1985, "*Alcaligenes eutrophus* CH34 is a facultative chemolithotroph with plasmid-bound resistance to heavy metals". J. Bacteriol. 162 328–334) controlling resistance against $Cd^{++}$, $Co^{++}$, $Zn^{++}$, $Hg^{++}$, $Tl^+$, $Cu_{++}$, $Pb^{++}$ (pMOL30, 240 kb) and $Co^{++}$, $Zn^{++}$, $Ni^{++}$, $Hg^{++}$, $CrO4^-$, $Tl^+$ (pMOL28, 165 kb) On pMOL28 nickel, cobalt and zinc genes (cnr) are [ . . . ] on the same cluster very near to the chromate genes (chr) One DNA fragment (in pMOL30) of about 9 kb (Nies D. et al., 1987, "Cloning of plasmid genes encoding resistance to cadmium, zinc and cobalt in *Alcaligenes eutrophus*" Bacteriol. 16, 4865–4868) is responsible for the resistance against cadmium, zinc and cobalt (czc). And another gene cluster seems to code for copper and lead resistance (cup). Both plasmids contain a mercury transposon: Tn4378 and Tn4380 (Diels L. et al., 1985, "Mercury transposons from plasmids governing multiple resistance to heavy metals in *Alcaligenes eutrophus* CH34", Arch. Int. Physiol. Biochim. 93, B27–B28; Diels L. et al., 1989, "Large plasmids governing multiple resistances to heavy metals: a genetic approach" Toxic. Environm. Chem. 23, 79–89). Different heavy metal resistances genes are cloned and sequenced, namely czc (Nies D. H. et al., 1989, "Expression and nucleotide sequence of a plasmid determined divalent cation efflux system from *Alcaligenes eutrophus*", Proc. Natl. Acad. Sci. USA 86, 7351–7356), cnr (Siddiqui R. A. et al., 1989, "Cloning of pMOL28-encoded nickel resistance genes and expression of the gene in *Alcaligenes eutrophus* and Pseudomonas spp", J. Bacteriol. 171, 5071–5078) and chr (Nies A. et al., 1990, "Nucleotide sequence of chr genes responsible for resistance to chromate in *Alcaligenes eutrophus*", J. Biol. Chem. 265, 5648–5653). From the copper and lead genes, mutants are available.

The czc and mercury genes were used as probes for hybridization with total DNA from strains isolated from different mining and industrial sites in Belgium and Zaire (Diels L. et al., 1988, "Isolation and characterization of resistant bacteria to heavy metals from mining areas of Zaire", Arch. Int. Physiol. Biochim. 96, B13; Diels L. et al., 1988, "Detection of heterotrophic bacteria with plasmid-bound resistances to heavy metals from Belgian industrial sites", Arch. Int. Physiol. Biochim. 96, B14). From these different sites, strains hybridizing with these probes could be isolated (Diels L. et al., 1990, "DNA probe-mediated detection of resistant bacteria from soils highly polluted by heavy metals" Appl. Environm. Microbiol. 5, 1485–1491).

As could be shown by Nies D. et al. (1989, "Plasmid determined inducible efflux is responsible for resistance to cadmium, cobalt and zinc in *Alcaligenes eutrophus*" J. Bacteriol. 171, 896–900 and 1989, "Metal ion uptake by a plasmid-free metal sensitive *Alcaligenes eutrophus* strain", J. Bacteriol. 171, 4073–4075) resistance to chromate is inducible and based on decreased net accumulation of the metal anion. Resistance to zinc, cadmium, cobalt and nickel are resulting from inducible, energy dependent cation efflux systems. In some physiological circumstances *Alcaligenes eutrophus* can also accumulate and precipitate heavy metals (Diels L., 1990, "Accumulation and precipitation of Cd and Zn ions by *Alcaligenes eutrophus* strains", Biohydrometallurgy (1989) 369–377; Diels L. et al., 1989, "Isolation and identification of bacteria living in environments severely contaminated with heavy metals", 7th International Conference on Heavy Metals in the Environment, Sep. 12–15, 1989, Geneva). At increased concentrations of Cd or Zn ions, a removal of these metals from the solution is observed during the late log phase and the stationary phase. This accumulation and precipitation is correlated with the concentration and kind of carbon source (lactate or gluconate), with the progressive alkalinization of the periplasmic space and the surrounding medium, due to the proton antiporter system of the resistance mechanism, with the concentration of phosphate and appears to be associated with the outer cell membrane. The precipitation of $CdCO_3$ and $Cd(OH)_2$ is proved by IR-spectroscopy. The interpretation of this feature is that the metal speciation will change at the cell surface due to the progressive pH increase, the steep pH gradient on this site, and the production of $CO_2$ by the cell metabolism.

For electrochemical purposes, membranes have been developed (Leysen R. et al., 1987, "The use of heterogeneous membranes in electrochemical systems", in "Synthetic polymeric membranes", Eds. B. Sedlacek and J. Kahovec, W. de Gruyter, Berlin) composed of a polymeric polysulfone material in which zirconium oxide grains are distributed in a homogeneous way in order to form a composite membrane; these membranes are formed using the phase inversion technique (evaporation—crystallization).

This type of membrane has already been produced in three different configurations: flat membranes (Doyen W. et al., 1988, "The use of $ZrO_2$-based composite membranes for the separation of oil-water emulsions", in Proceedings of the Symposium on "Particle Technology in relation to Filtration Separation", Antwerp, October 3–4) with or without a reinforcing support, hollow fibers (Matthys J. et al., 1989, "Development of hollow fibers for the production of secretory products by living cells, in Proceedings of the Symposium on "Down stream processing in Biotechnology", Bruges, April 10–11) and tubes (Doyen W. et al., 1989, "New composite tubular membranes for ultrafiltration" in Proceedings of the "6th International Symposium on Synthetic Membranes in Science and Industry", Tübingen, September 4–8); however, the hollow fibers (when their diameter is smaller than about 4 mm) are very sensitive to clogging especially in the presence of an effluent which contains suspended materials.

SUMMARY OF THE INVENTION

An aspect of the invention is to provide membranes with immobilized microorganisms thereon and/or therein, enabling elimination of low metal concentrations, particularly of heavy metals.

Another aspect of the invention is to provide membranes with immobilized microorganisms on and/or in said membranes, enabling degradation of xenobiotic organic compounds.

Advantageously, biofilms formed by the microorganisms on the membranes of the invention are used to eliminate metals and/or to degrade xenobiotic organic compounds.

Another aspect of the invention is to provide membranes with immobilized microorganisms thereon and/or therein, enabling synthesis of compounds when the microorganisms contain the appropriate cellular machinery.

The membranes of the invention with immobilized microorganisms thereon and/or therein are characterized by the fact that the microorganisms are alive or in a viable form and are liable to or effective to precipitate one or several metals, when they are in the presence of said metal and/or to degrade xenobiotic organic compounds, when they are in the presence of said compounds. The membranes are of porous material, said material being either an inorganic oxide or a composite material containing an inorganic oxide and an organic polymer, preferably a polysulfone, the membrane being such that the microorganisms can settle in the pores, said pores communicating between themselves, so that it makes it possible an appropriate colonization of the membranes by the microorganisms, and such that the release of the microorganisms is not significant and advantageously less than about $10^4$ microorganisms/ml/h, preferably less than about $10^2$ microorganisms/ml/h.

An important feature of the membranes of the invention is the fact that the size of the pores is appropriate to the size of the microorganism which is immobilized in the membrane, i.e. large enough for the microorganisms to settle and to grow and not too large to prevent the release of said microorganisms, especially in the effluent to be treated.

By "microorganisms", one may cite, for instance, bacteria, algae, yeasts, fungi. Bacteria are advantageously used for the membranes of the invention.

Another aspect of the invention is to provide with a biofilm obtained with immobilized microorganisms on and/or in said membrane, enabling for separation of the effluent to be treated from the nutrient medium necessary for the life of microorganisms, i.e. enabling recovery of a non contaminated effluent. The microorganisms grow through the membrane and penetrate the skin side via cracks of the skin side of the membrane, the biofilm being formed in the cracks from the microorganisms and spread on the surface of the membrane.

Another aspect of the invention is to provide reactors including membranes with immobilized microorganisms thereon and/or therein enabling treatment of effluents contaminated with metals, said effluents being separated from the nutrient medium necessary for the life of the microorganisms.

Another aspect of the invention is to provide reactors having both a good metal removal capacity and a reduced need for the concentration of nutrients. Such Reactors can contain a Flat Sheet membrane (hereafter designated by FSR) or a Tubular Membrane (hereafter designated by TMR), and can be installed in a Continuous installation (hereafter designated respectively by CFSR for Continuous Flat Sheet Reactor and CTMR for Continuous Tubular Membrane Reactor).

The invention relates to installations wherein a recovery column is integrated downstream of reactor, said column being such that it enables recovery of metal which has been precipitated together with bacteria involved in said precipitation, said column being preferably filled with a material liable to or effective to adsorb metal and bacteria, such as glass beads, glass wool, glass powder or other form of silicate like sand particles.

In order to recover the biologically precipitated metals, a recovery column can be integrated in the circuit downstream of the FSR, CFSR, TMR, or CTMR installation.

Bacteria are released slowly from the reactor into the effluent, where they interact with the metals around them and afterwards they must be removed from the suspension. For this a column, preferentially filled with glass beads, glass wool or glass powder, or other silicate like sand particles, is installed downstream of the reactor. The bacteria together with the crystallized metals can bind to the glass beads, the glass wool or glass powder, or other materials of the column. When the column is completely filled and saturated with metals, it can be replaced by another column without causing problems at the level of the membrane in the reactor. The metals can be eluted from the column by acids (this eluate can be used for metal recovery by electrolyses), and the column, regenerated in this way, can be reused.

The invention also relates to a process for precipitating metals or degrading xenobiotic organic compounds wherein a nutrient is administered into one of the chambers of the reactor according to the invention, and effluent to be treated containing metals or xenobiotic organic compounds are circulated in the other chamber of said reactor and wherein the bacteria in and on the membrane induce either precipitation and crystallization processes which results in the settling of the metals, or mineralization of xenobiotic organic compounds, or by co-metabolism of said xenobiotic compounds in the presence of a substrate, which results in degradation of said xenobiotic organic compounds into water, $CO_2$ and a mineral salt originating from the inorganic ions of said xenobiotic organic compounds and of said substrate, said process for precipitating metals or degrading xenobiotics being carried out continuously or in batch.

The invention also relates to a process for precipitating metals, wherein the bacteria come into contact with the metals in solution, and induce the precipitation and crystallization of the metals around them. Advantageously, said bacteria are recovered together with crystallized metals by a column downstream of the reactor.

The invention also relates to a process for degrading xenobiotic organic compounds, wherein a substrate for induction of co-metabolism is used for the mineralization of xenobiotics by the bacteria into water, $CO_2$ and either inorganic salts originating from inorganic ions of said xenobiotic organic compounds and of said substrate or gas, or wherein no substrate is used and xenobiotic organic compounds in the solutions to be treated are mineralized into water, $CO_2$ and possibly $Cl^-$ (in the case of chlorinated compounds) by the bacteria.

Another aspect of the invention is to provide with reactors having both a good metal removal capacity and a reduced need for the concentration of nutrients.

PREFERRED EMBODIMENTS OF THE INVENTION

The membranes with immobilized microorganisms, especially bacteria, thereon and/or therein according to the invention can be used to remove metals if the bacteria can induce the accumulation and/or the precipitation of said metals when the latter are in a solution (hereafter called "effluent"), when said effluent is in the presence of said membranes.

Accumulation corresponds to the adsorption of the metals on the sites of the bacteria, said sites being on the bacterial walls or at the extracellular polymers of said bacteria walls.

The precipitation of the metal takes place on the bacterial walls, as well as on the membranes and in the vessel in which the membranes can be located.

By metal, one designates the transition metals, the rare earth, the elements having metallic properties in the families IIIa, IVa, Va and VIa of the periodic table.

By metals, one may cite for example cadmium, zinc, cobalt, copper, lead, mercury, thallium, chromium and manganese in the form of salts, either in a soluble or non soluble state.

The expression immobilized microorganisms on and/or in the membrane means that the microorganisms are trapped in the pores of the membrane, but can migrate from one pore to another one, especially if space is needed after cellular division.

When the membrane has immobilized microorganisms thereon and/or therein, the microorganisms can migrate in the direction of the nutrient medium in the presence of which the membrane can be.

The microorganisms on and/or in the membranes must be non killed, i.e. alive or liable to or able to be brought back to life, for instance lyophilized, in so far as the lyophilization process does not destroy most of the microorganisms.

The membranes are such that the release of bacteria is less than about $1 \times 10_4$ cells/ml/h, preferably less than about $1 \times 10_2$ cells/ml/h.

For heavy metal removal, a direct contact between the metals and the bacteria is necessary to induce metal precipitation and crystallization.

When there is substantially no cell release from the membrane, the metal moves to the immobilized cells and precipitates around them. This results in crystal growth in and on the membrane. With this system heavy metal removal is also very slow. And once the membrane is saturated, an acid treatment can be carried out to regenerate the membrane, but with the risk of eliminating all viable immobilized cells.

When there is indeed cell release, the metals come immediately in contact with the bacteria around which they crystallize. This is a faster process and gives no membrane regeneration problems. Besides, the bacteria with crystallized metals must be removed by a recovery column (such as a glass bead column). When no more metal is available, the free bacteria will bind with much difficulty to the recovery column; this means that cell release must be steered or modified as a function of metal concentration. The cell release can be influenced by the diameter of the skin pores of the membrane or by the pump flow rate in the effluent at the membrane.

If the release is above these values, there is a contamination of the effluent containing the metal or organic compound to be eliminated.

The membranes with immobilized bacteria thereon and/or therein can also be used to degrade xenobiotic organic compounds, if the microorganisms have the genes responsible for the degradation or mineralization of these compounds and if they can express them.

The xenobiotic organic compounds designate the compounds which may endanger health and which are man made chemicals (non naturally occurring compounds). By way of example, one may cite fungicides, herbicides, pesticides, insecticides, chloroorganic compounds, particularly biphenyl compounds.

The membranes of the invention can enable elimination of up to about 90% of metals contained in an effluent to be treated or up to about 90% of xenobiotic organic compounds contained in an effluent to be treated.

The membranes according to the invention contain pores at its surface and in its thickness in which the microorganisms can nest and grow, which implies that the pores must be large enough for the size of the microorganisms and must not be too large otherwise the microorganisms would be released from the pores. The pores in the skin serve as an anchoring means for the biofilm.

An advantageous group of membranes with immobilized bacteria thereon and/or therein is constituted by the membranes in which the pores of the membranes have a maximum size of about $1\mu$ at the skin side (hereafter defined) and between about $1\mu$ and about $5\mu$ at the other side.

An advantageous group of membranes with immobilized bacteria thereon and/or therein of the invention is constituted by membranes wherein the porosity is of about 50% to about 80%, preferably of about 65% to about 75%.

The porosity is defined by the ratio between the volume of the pores and the volume of the total material which constitutes the membranes.

The thickness of the membranes must advantageously be such that there is appropriate tightness between the two parts located respectively on each of the sides of the membrane, said parts being created by the division of the space, by the membranes.

When the membranes are thicker (i.e. more than about 200μ), the surface of the membranes can be smaller, for the same results of elimination of metals or xenobiotic organic compounds.

Moreover, in the case of thicker membranes, i.e. of more than about 200μ, the release of the bacteria is smaller. To give an idea, a thickness of about 250μ reduces the release of microorganisms by about 10 times compared to a membrane of about 60μ.

Besides, when the membranes are thicker, i.e. more than about 200μ, there is a good accumulation of the metal on the membrane. To give an idea, a thickness of about 250μ enables to increase the accumulation of metal of about 5 times with respect to a membrane of about 60μ.

The thickness of the membranes is an important aspect, especially when the metal concentration is low.

In fact, when the metal concentration is low, i.e. of less than about 1 ppm, the precipitation does not work very well, and the fact that the metal can accumulate on the bacterial wall plays an important part in the efficiency of the metal removal. To give an idea, 50% of a metal can be eliminated from a solution containing 0.5 ppm of said metal.

Advantageous microorganisms used are bacteria. An advantageous group of bacteria is *Alcaligenes eutrophus* CH34 (ATCC No 43123), which can be used to precipitate one or several heavy metals such as zinc, cadmium, nickel, lead and copper. Another advantageous bacteria is A5 (deposited at the C.N.C.M., Institut Pasteur, 28 rue du Dr Roux, 75015 Paris, on Feb. 28, 1991, under No. 1-1047), which is effective to degrade xenobiotic organic compounds.

The membranes of the invention enable thus removal of up to about 225 ppm of cadmium, up to about 720 ppm of zinc, up to about 150 ppm of nickel up to about 150 ppm of lead, and up to about 60 ppm of copper. The lowest concentrations which can be removed are at least in the order of 1 ppm.

Advantageously, the membranes with immobilized microorganisms, particularly bacteria, thereon and/or therein are such that the thickness of the membranes is of about 50μ to about 700μ, preferably of about 70 to 500μ, and more advantageously of about 250μ to about 500μ.

Preferably, the membranes with immobilized microorganisms, especially bacteria, thereon and/or therein according to the invention are substantially homogeneous in the whole of their thickness.

Said homogeneity corresponds both to the fact that the pores are substantially equally distributed in the membrane and to the fact that the size of the pores is substantially the same. It is advantageous that the membrane should not contain large pores or finger like structures (i.e. pores of over 10μ), to prevent significant release of bacteria. It is also advantageous that the pores are not finger like shaped, because the trapping of microorganisms is not good, and consequently, release can be enhanced.

According to an advantageous embodiment of the invention, one of the sides of the membrane form a skin having pores, the size of which prevents the bacteria from being released, the size of these pores being advantageously smaller than about 1μ, and preferably smaller than about 0.5μ. The side of the membrane which contains the smaller pores is hereafter named the "skin side".

Advantageously, the membrane is made of polysulfone including an inorganic material, such as $ZrO_2$, $Sb_2O_3$, and $Al_2O_3$, alone or in combination. The inorganic material can assist the formation links between the bacteria and the membrane or the adhesion of the bacteria to the membrane.

The membranes used are for instance described in European Patent Application No 241995.

Pore formers such as $Sb_2O_5$, $CaCO_3$, ZnO or polyvinylpyrrolidone (PVP) can be added during the manufacture of the membrane for the production of pores, but are eliminated at the end of the production process of the membrane.

Preferred membranes have the following composition:
about 80% ZrO2,
about 20% polysulfone.

Other preferred membranes are made of inorganic materials, such as inorganic oxides, such as one or more of $ZrO_2$, $Sb_2O_3$, and $Al_2O_3$.

In these cases, the material of the membranes is designated by ceramics.

Pore formers such as $CaCO_3$, ZnO, or polyvinylpyrrolidone (PVP) can be added with polysulfone during the manufacture of the membrane for the production of pores, but are eliminated at the end of the production process of the membrane by acid leaching.

According to another advantageous embodiment of the invention on one of the sides of the membranes, externally, the bacteria are in the form of a biofilm of a thickness of about 1 to about 50μ, preferably of about 10 to about 20μ and internally the bacteria form a colonizing front, around single dispersed bacteria in the membrane. The biofilm is always located externally on one of the sides of the membranes, but it is not always present. The biofilm can be defined as a mass of bacteria which are fixed to each other by their own polymers. The biofilm results from the growth of the bacteria, which have previously been introduced into some pores on the surface of said membrane. The biofilm is formed in cracks of the skin side of the membrane, from the microorganisms growing through the membrane. Such cracks inherently exist on the skin of membranes of the type used. The biofilm extends from these cracks onto and across the surface of the membrane.

The colonizing front is always present in the membranes and it corresponds to the filling of the pores by the bacteria, said colonizing front extends from one side of the membrane and have a thickness of about 10μ, preferably 50μ, to about the totality of the thickness of the membrane.

The growth of the microorganisms can be controlled by the nutrient medium and by the supply of oxygen.

After being introduced into some of the pores of the membrane, in the membrane and on the surface of the membrane, the bacteria grow inside the membrane, and on its surface, provided the size of the pores enables it and provided the pores communicate between themselves.

When the membrane includes a skin side, the biofilm is on the skin side.

As to the colonizing front, it is inside the membrane and limited to the membrane thickness.

To give an idea, when the growth of the bacteria on the membrane has been monitored such that the biofilm is on the skin side, outside the membrane, the colonizing front can have a thickness of about 10μ, preferably 50μ, to about the totality of the thickness of the membrane, and preferably of about 100μ to about 200μ.

Advantageously, the microorganisms are liable to or effective to precipitate one or several metals, when they are in the presence of said metal and/or to degrade xenobiotic organic compounds, when they are in the presence of said compounds, or to synthesize compounds when a substrate to be transformed is present.

Figure 1:
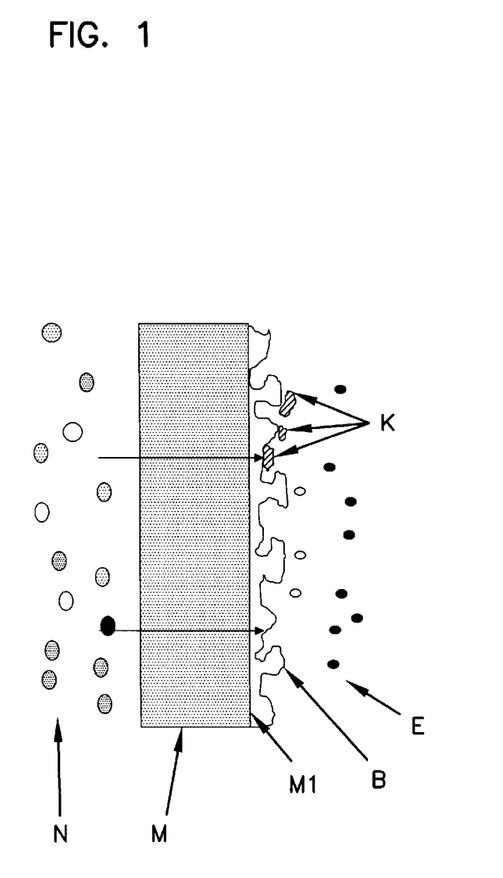
FIG. 1 shows the precipitation of metal crystals by a biofilm of microorganisms immobilized in and/or on a membrane.

FIG. 1 shows an organo-mineral membrane M with a biofilm B to precipitate metal crystals K. The biofilm is at the waste water side M1 (skin side). Nutrients N, carbon, nitrogen, phosphor or sulfur diffuse through the membrane M (as indicated by arrows) and stimulate the microbial activity in the biofilm B, to produce carbonates, to create a pH gradient, and to form metal binding proteins.

Figure 2:
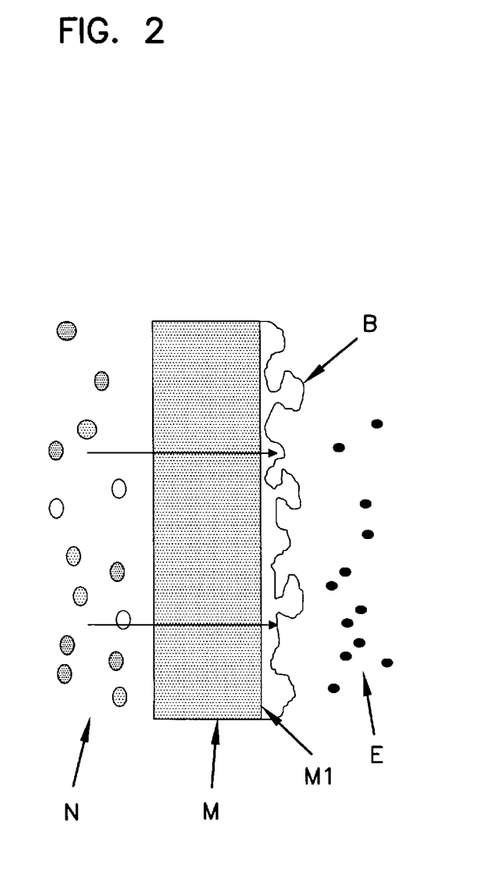
FIG. 2 shows the degradation of organic xenobiotics by a biofilm of microorganisms immobilized in and/or on a membrane.

FIG. 2 shows an organo-mineral membrane M with a biofilm B at the waste water side M1 (skin side) to biodegrade organic xenobiotic compounds. Nutrients N (nitrogen, phophor and sulfur) diffuse through the membrane M and stimulate the microbial activity in the biofilm B, to produce the enzymes that degrade the organic compounds. Carbon is only added in the colonization period of the reactor in order to develop the biofilm on the skin side M1 by bacterial transport through the membrane M. In case of very small xenobiotic contaminant concentrations, some carbon source can also be added via the nutrient.

The membranes with bacteria immobilized thereon and/or therein are advantageously used in new reactors.

The reactors of the invention are new, not only because of the membranes used, but also because they correspond to a new configuration, in so far as these reactors include two chambers corresponding respectively to the effluent to be treated and to the nutrient medium, said two parts being created in the cell of the reactor by the separation of said cell with an appropriate membrane.

Said reactors of the invention are cells containing:
  a membrane with immobilized microorganisms thereon and/or therein, especially bacteria, said microorganisms being alive or in a viable form, said membrane being of a porous material such that the microorganisms can settle in the pores, said pores communicating between themselves so that it makes it possible an appropriate colonization of the membrane by the microorganisms, and such that the release of microorganisms is not significant,
  possibly a support,
  two chambers with each an inlet and an outlet and separated by a membrane, one of the two parts being in contact with one side of the membranes, and containing a nutrient medium to enable the life and growth of the microorganisms, and the other one, being in contact with the other side of the membranes and containing an effluent to be treated.

The expression "appropriate colonization" means that, after the incorporation of the bacteria in the pores of the membrane and due to the growth of the bacteria, the pores of the membranes can be filled by bacteria in a sufficient amount for the process to be efficient. An efficient process is a process in which the bacteria can grow on the membrane and exert their function at the outside of the membrane (being the effluent side) in a biofilm.

Figure 3:
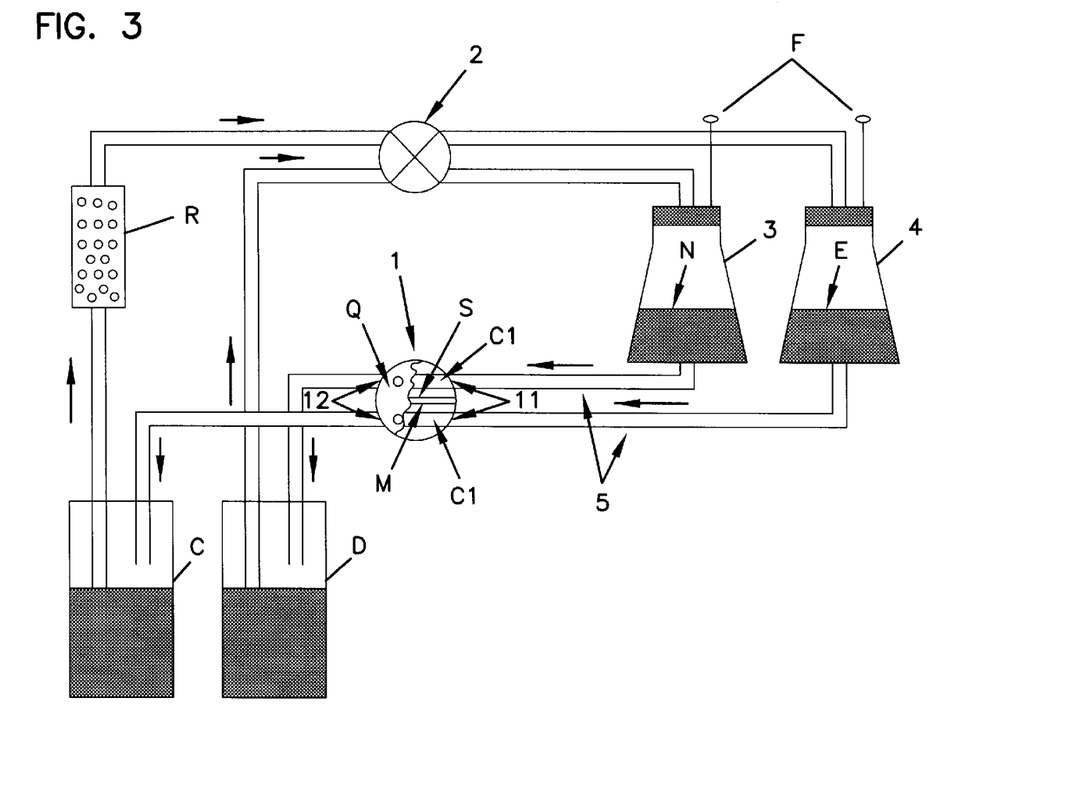
FIG. 3 represents a continuous installation to implement a reactor including a flat sheet membrane (CFSR) according to the invention.

To implement a reactor according to the invention, an installation as shown in FIG. 3 can be used. It includes a reactor 1, the cover Q of which being partially removed, consisting of two chambers C1, C2, with each an inlet 11 and outlet 12 and separated from each other by a flat membrane M and a supporting frame S. In one chamber C1 nutrient solution N is pumped by a pump 2 from a receiver 3 during reactor use, and at the other chamber C2 a synthetic or a real effluent solution E is pumped by the pump 2 from a receiver 4. Receivers 3 and 4 are aerated by air filters F. A double circuit loop 5 links the pump 2, the receivers 3, 4 and the cell 1 to siphons C, D. The nutrient and effluent solutions follow the stream indicated by the arrows. With this system a reduction of nutrients can be obtained. A recovery column R is advantageously installed downstream of the siphon C. The siphons C and D are used to keep the pressure difference over the membrane at zero.

The effluent to be treated is advantageously a continuous flow. The flat membrane reactor is used as a Flat Sheet Reactor (FSR) or a Continuous Flat Sheet Reactor (CFSR) when the effluent is a continuous flow.

The conditions in the reactor above referred to are:
  the composition of the nutrient medium,
  the amount of the nutrient medium,
  the amount of oxygen,
  the ratio of nutrient volume to effluent volume,
  the flow rate of the effluent volume and
  the flow rate of the nutrient medium.

The flow rate of the effluent medium must not be too high so that too many microorganisms are not released into the effluent medium.

An advantageous flow rate of the effluent medium is of about 1 ml/s/cm$^2$ to about 4 ml/s/cm$^2$, preferably of about 2 ml/s/cm$^2$.

As to the nutrient medium, it can be or not continuous and its flow rate can preferably vary from about 10 $\mu$l/s/cm$^2$ to about 200 $\mu$l/s/cm$^2$, preferably of about 0 to about 100 $\mu$l/s/cm$^2$.

An advantageous ratio between the volume of nutrient medium with respect to the volume of the effluent is about 1/10 to about 1/1000.

By way of example, in a reactor of the invention, the effluent volume is about 5 l and the nutrient medium volume is of about 500 ml, for a surface membrane of about 10 cm$^2$.

The effluent must have a pH such that it does not kill the microorganisms.

The effluent must be previously treated so that the pH is about 6 to about 8, preferably about 7 to about 7.5.

The effluent must contain no organic solvent in an amount liable or effective either to kill the microorganisms or to dissolve the membrane. The organic solvent, if any, must be under about 5% (expressed in weight).

In the nutrient medium, it must be taken into account the fact that the immobilized microorganisms need less nutrient elements than when they are free.

The amount of the nutrient medium needed for the immobilized bacteria is about 10 times less than the amount of nutrient medium needed for the free microorganisms.

The nutrient medium includes:
  a carbon source,
  a phosphate,
  a nitrogen.

As a carbon source, one may use lactate or acetate.

Lactate is advantageously used, in an amount of about 1 g/l for 10$^9$ bacteria/ml, i.e. about 0.1 g/l for 10$^8$ bacteria/ml. This corresponds to about 0.3 g/l of effluent.

The phosphate used is advantageously under the form Na$_2$HPO$_4$.

It is used in a concentration of about 1 mM for 10$^9$ bacteria/ml, i.e. 0.1 mM for 10$^8$ bacteria/ml. This corresponds to about 0.02 mM/l of effluent.

The nitrogen used is advantageously under the form of nitrate.

It is used in a concentration of about 1 mM for 10$^9$ bacteria/ml, i.e. 0.1 mM for 10$^8$ bacteria/ml. This corresponds to about 0.2 mM/l of effluent.

The pH of the nutrient medium is advantageously from about 7.5 to about 9, and is advantageously about 7.8.

The shape of the membrane must be such that it forms a surface liable or effective to be a separation for the two different chambers C1 and C2 located respectively on each side of the membrane.

Advantageously, the surface of the membrane is flat or tubular, with or without the support S.

When the membrane is flat, its size can be of about 10 cm$^2$ to about 1 m$^2$.

Figure 4:
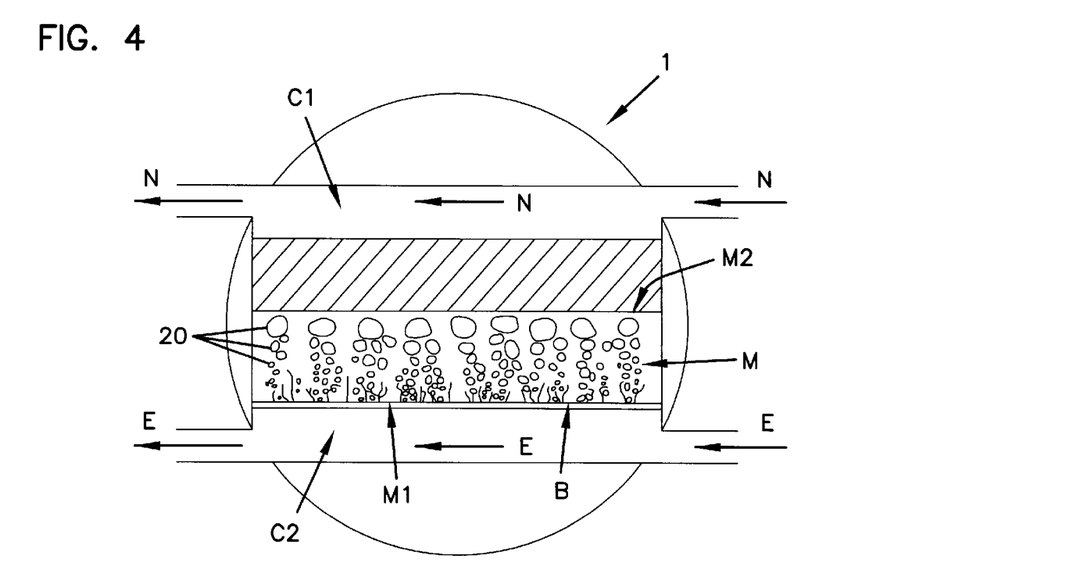
FIG. 4 represents a cross section of the reactor according to FIG. 1, in parallel with the plane of that Figure.

The cross section of the reactor 1, as represented in FIG. 4, shows schematically the flat membrane.

The membrane flat M, advantageously combined with the support S which prevents the membrane from being torn in case the membrane, is subjected to high pressures, or to pressure differences between the two chambers located respectively on each side of the membrane.

It is advantageous to combine a support on either side of the membrane, or on both sides of the membrane. Said support has substantially the surface size of the membrane and has a thickness of about 100$\mu$ to about 1000$\mu$, and is provided with holes of about 50$\mu$ to about 500$\mu$, preferably of about 100$\mu$. Said support is advantageously adjacent to the membrane. Said support is advantageously constituted of the following material: polyester with a pore diameter between about 10$\mu$ to about 200$\mu$.

There is advantageously a biofilm B of microorganisms, particularly bacteria, located on the side of the membrane M which has the smaller pore size, i.e. on the skin side M1, as schematically indicated in FIG. 4 by the decreasing size of the pores 20 from the open side M2 to the skin side M1.

The bacteria receive nutrients in the biofilm B by nutrients diffusing from the chamber C1 communicating with the nutrient circuit in the reactor 1, through the support S and the membrane M to the biofilm B. In that way, the precipitation of heavy metals from the chamber C2, which communicates with the effluent circuit in the reactor 1, is induced to the biofilm of bacteria.

More generally, an advantageous reactor of the invention includes a flat membrane with immobilized microorganisms, especially bacteria, thereon and/or therein according to the invention, said membrane separating two chambers with each an inlet and an outlet, one of the chambers containing nutrient medium and the other chamber containing an effluent to be treated.

The chamber containing the nutrient medium can be either in contact with the side of the membrane with the smaller pores or can be in contact with the side of the membrane with the larger pores.

When there is a biofilm, it can be either in contact with the effluent or in contact with the nutrient medium.

Advantageously, the chamber containing the effluent medium is in contact with the skin side of the membrane and the chamber containing the nutrient is in contact with the side of the membrane with the larger pores.

Advantageously, the biofilm of bacteria is located externally on the side of the membrane with the smaller pores, and the biofilm is in contact with the effluent.

In this case, the bacteria are immobilized, preferably by tangential filtration of a suspension of bacteria introduced into one of the chambers.

The suspension of bacteria must be introduced into the chamber which is in contact with the side of the membrane with larger pores, i.e. opposite to the skin side.

The suspension of bacteria is introduced either into the chamber which is destined to receive the effluent, after immobilization of the bacteria on the membrane or into the chamber which is destined to receive, after immobilization the nutrient medium, depending on the orientation of the skin side.

During the immobilization, it is not necessary that the bacteria be in the presence of a nutrient medium.

When the immobilization of the bacteria is over, colonization is carried out in the presence of a nutrient medium which diffuses to the bacteria immobilized. When the colonization is over, the effluent to be treated is introduced into one of the chambers to receive it.

In one chamber nutrient solution is pumped during reactor use and at the other side an effluent solution is pumped. With this system a reduction of nutrients can be obtained.

Bacteria immobilized on and/or in the membrane are fed by nutrients coming from the nutrient side. At the effluent side the immobilized microorganisms remove the heavy metals from the effluent. Siphons are used to keep the pressure difference over the membrane at zero.

The leakage between the nutrient medium and the effluent is prevented in so far as the amount of nutrient medium is such that it is taken up by the microorganisms immobilized in and/or on the membrane.

The leakage between the effluent and the nutrient medium can be avoided by keeping in a constant way, low concentrations of nutrients, in the nutrient solution.

Figure 5:
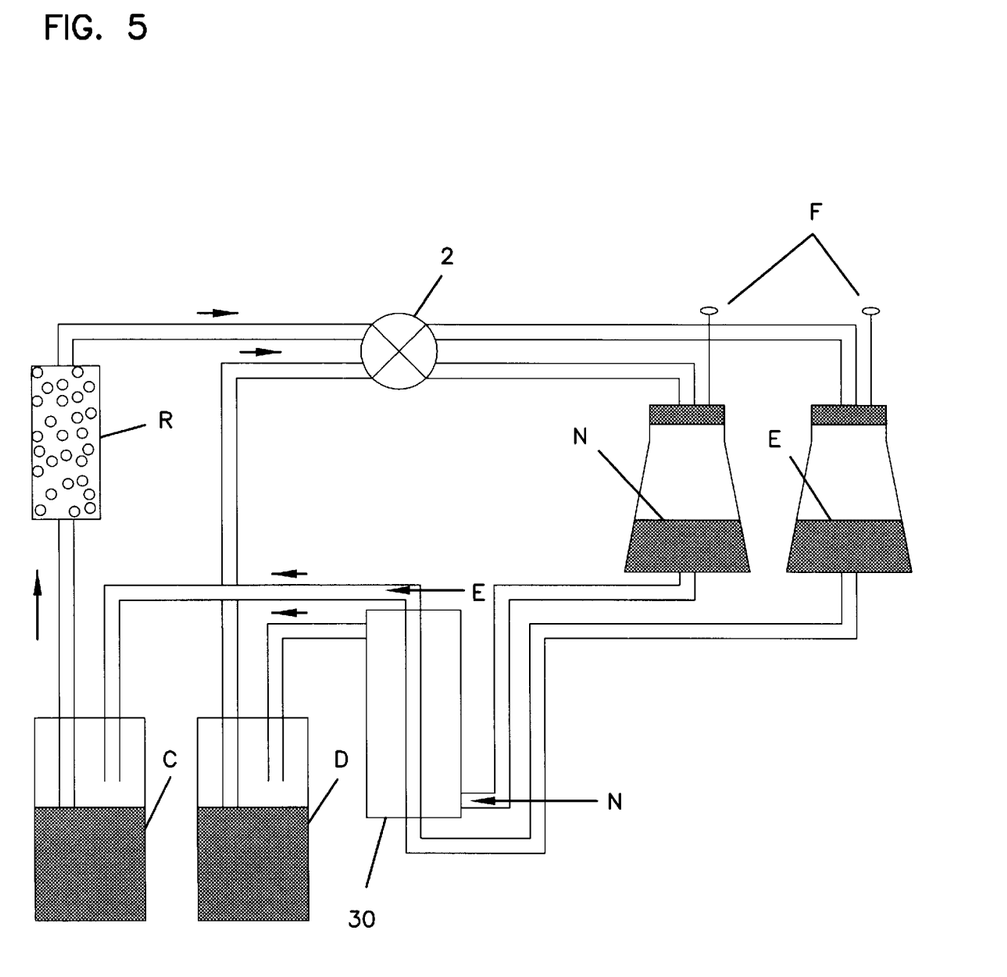
FIG. 5 represents an installation to implement a Tubular Membrane Reactor (TMR).

Another advantageous reactor according to the invention includes a tubular membrane. FIG. 5 shows an installation implementing a tubular membrane reactor (TMR) containing a tubular membrane. This installation is substantially identical to the installation shown in FIG. 1 except for the connections of the tubular reactor 30 at the outer shell side, "interlumen connection", with the nutrient circuit C and at the inner tubular membrane side, interlumen connection, to the effluent circuit E. The siphons C and D still regulate the pressure difference and, downstream of the reactor, a recovery column R is advantageously installed.

Figure 6:
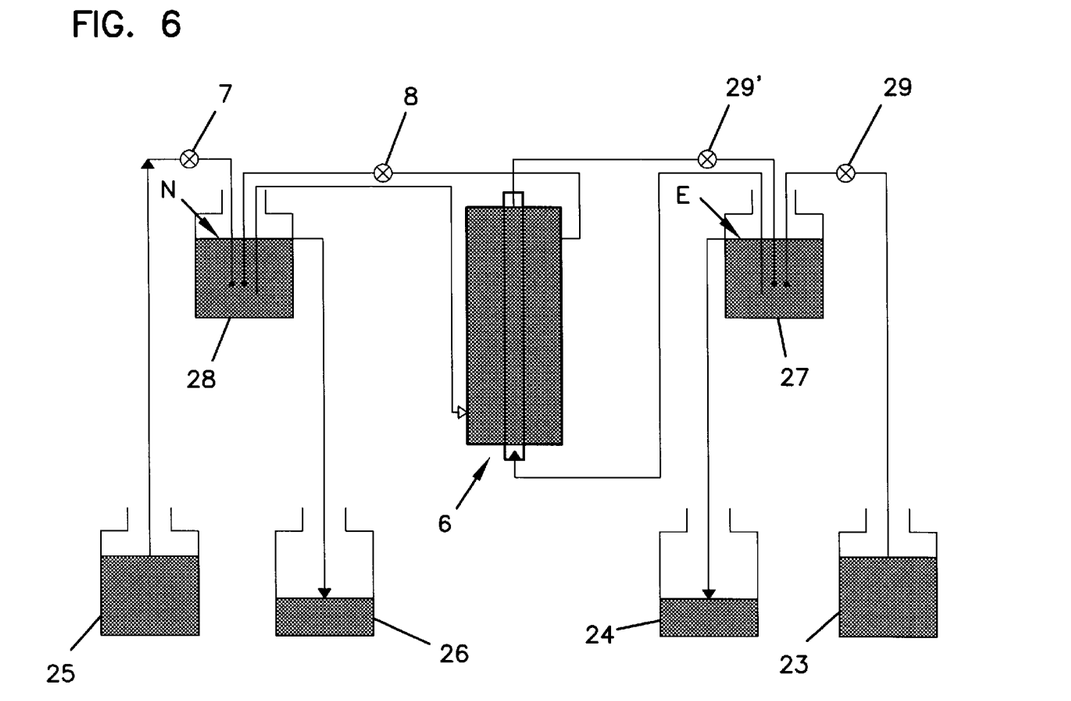
FIG. 6 represents a continuous installation to implement a tubular membrane reactor (CTMR) for the degradation of organic xenobiotics.

FIG. 6 represents a Continuous Tubular Membrane Reactor (CTMR) installation for the degradation of organic xenobiotics.

The installation consists of an input 23 and an output 24 with a metal contaminated waste water, and a nutrient input vessel 25 and a nutrient output vessel 26. As well for the waste water as for the nutrient N, the stream flows first to a conditioning vessel, respectively 27 for the effluent and 28 for the nutrient. A pump 29 pumps the waste water effluent E into the conditioning vessel 27 and a pump 29' pumps the waste water effluent through the tubular membrane reactor 6. A pump 7 pumps the nutrient into the nutrient conditioning vessel 28 and a pump 8 pumps it further through the tubular membrane reactor 6.

Figure 7:
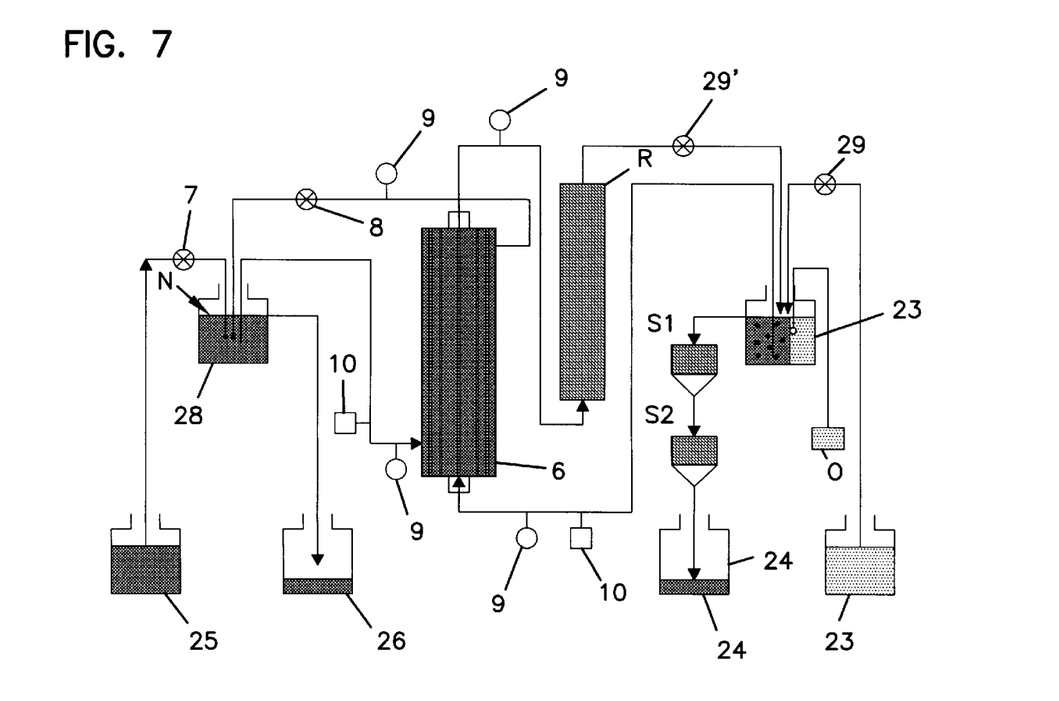
FIG. 7 represents a continuous installation to implement a tubular membrane reactor (CTMR) for the recovery of heavy metals.

FIG. 7 represents a Continuous installation to implement a Tubular Membrane Reactor (CTMR) for the recovery of heavy metals. This installation resumes the installation shown in FIG. 6, with the addition of a pressure measure device 9 at nutrient N and effluent E sides, at the bottom and at the top of the reactor 6, and a pressure regulation device 10, at the bottom of the reactor for nutrient and effluent sides. At the effluent conditioning vessel 27, oxygen, pH, redox and temperature are measured and oxygen or air provided 0. Metal crystals, formed by the microorganisms, are recovered on a metal recovery column R, filled with glass beads. Fine crystallites are recovered by filtration over two sand filters S1 and S2.

Figure 8:
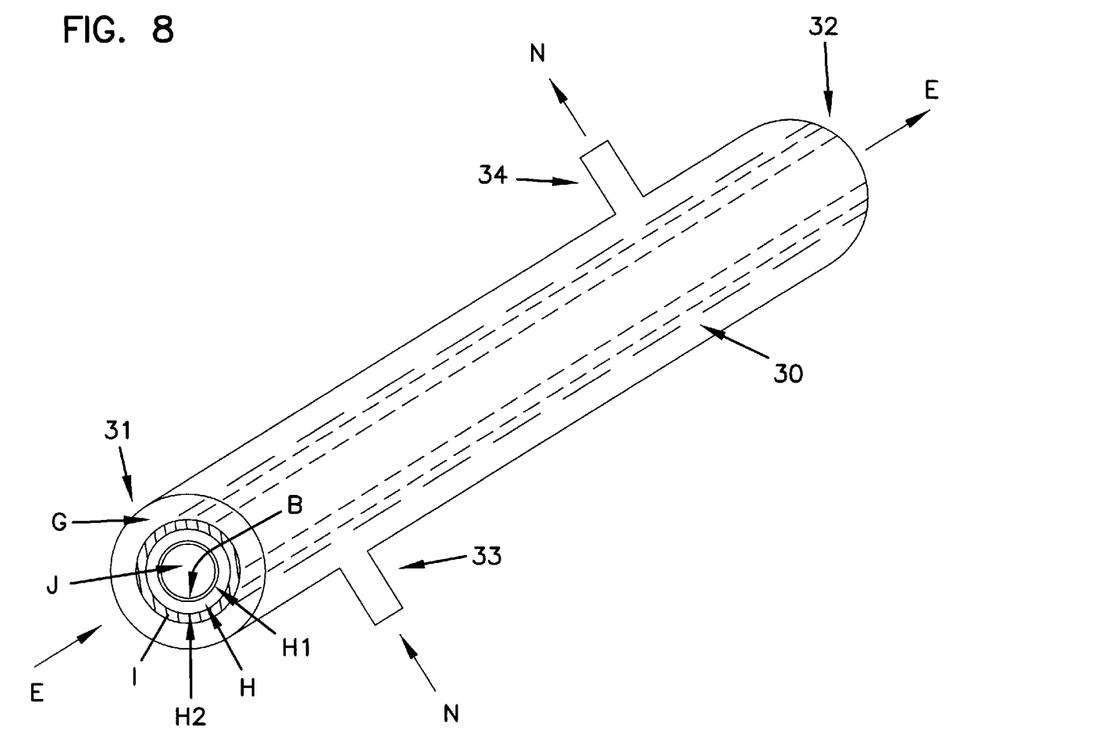
FIG. 8 represents an example of a tubular membrane of a Tubular Membrane Reactor (TMR).

FIG. 8 shows an example of a tubular reactor containing a tubular membrane which can be used in a TMR. Such a tubular reactor 30 includes an organo-mineral membrane H with a biofilm B on it, at the inner side of a support I. The effluent or waste water E flows through the inner tubular space interlumen J from inlet 31 to outlet 32. The nutrient N flows through the outer tubular space intralumen G from inlet 33 to outlet 34.

The colonizing front of bacteria is on the internal (or skin) side H1 of the membrane H, and can move from the internal part of the open side H2 of the membrane H up to the internal side H1.

Advantageously, when the membrane is tubular, the colonizing front is close to the internal side H1 of the membrane H which has the smaller pore size.

The tubular membrane is advantageously supported by a tube, such as the support I, and can be located either on the external surface of said tube or on the inner surface of said tube.

The tubes used are porous tubes, preferably carbon tubes or polyester tubes.

An advantageous multitude tubular membrane reactor can be realized with such tubes of the invention. It includes:

a tubular housing, said housing containing hollow tubes of a porous material, preferably carbon tubes, the inner surface or the outer surface of the carbon tubes being coated with a membrane according to the invention, said membrane being in contact with the effluent to be treated, the thickness of the carbon tubes being such that the microorganisms can be immobilized in the membranes by filtration of a suspension of microorganisms substantially along the outer or the inner surface of the tubes, and such that the nutrient medium which is either in the tube or in the intertubular space can diffuse from the outer or the inner surface of the tube respectively to the inner or to the outer surface of the tube coated with the abovesaid membrane.

In this embodiment, the membrane with immobilized microorganisms, especially bacteria, thereon and/or therein can be on the outer surface of the tubes.

In these conditions, the side of the membrane having the skin side is preferably opposite to the side of the membrane which is in contact with the outer surface of the tube.

In this embodiment, the effluent to be treated is in the intertubular space and the nutrient medium is inside the tube.

In this case, the microorganisms have been immobilized, preferably by tangential filtration, along the inner surface of the tubes, of a suspension of bacteria.

When the membranes are tubular and coat the inner surface of the tube and have a skin side, the larger size pores are preferably in contact with the inner surface of the tube and the colonizing front is preferably close to the skin side, inside the membrane.

Advantageously, the membrane with immobilized bacteria thereon and/or therein coat the inner surface of the tube. In these conditions, the side of the membrane having the skin side is preferably opposite to the side of the membrane which is in contact with the inner surface of the tube.

In this embodiment, the effluent to be treated is preferably inside the tube and the nutrient medium is in the intertubular space.

In this case, the bacteria have been immobilized preferably by filtration, along the outer surface of the tube, of a suspension of bacteria.

Another advantageous reactor of the invention includes:

a tubular recipient, said housing containing supporting tubes of a porous material, said supporting tubes being carbon tubes or polyester tubes, the inner surface of the supporting tubes being coated with a membrane according to the invention, said membrane being in contact with the effluent to be treated, the thickness of the carbon tubes being such that the microorganisms can be immobilized in the membranes by filtration of a suspension of microorganisms substantially along the outer surface of the tubes, and such that the nutrient medium which is in the intertubular space can diffuse from the outer surface of the tube respectively to the inner surface of the tube coated with the abovesaid membrane.

Preferably, the thickness of the carbon tube is about 1 to about 3 mm, and the thickness of the polyester tubes is about 100 to about 500$\mu$.

In this embodiment, the bacteria are first immobilized by a filtration of a suspension of bacteria tangentially along the outer surface of the tube, said bacteria going through the supporting tube and settling in and/or on the membrane. Then, the introduction of a nutrient medium in the intertubular space, which diffuses through the tubes to the membrane allow the bacteria to grow up to and on the skin side, forming a colonizing front from microcolonies around single dispersed bacteria and thus a biofilm at the skin side.

Then the effluent to be treated can be introduced into the inner surface of the membrane, through the tube.

The nutrient medium can also be inside the inner surface of the membrane and the effluent medium can also be in the intertubular space.

The invention also relates to a reactor according to the invention, including a tubular housing, said housing containing supporting tubes of a porous material, said supporting tubes being carbon or polyester tubes, the inner surface of the supporting tubes being coated with a membrane according to the invention, said membrane having preferably its larger pores in contact with the inner side of the tubes and said membrane having preferably its smaller pores in contact with an effluent medium and including preferably an internal biofilm close to the side of the smaller pores, the intertubular space being preferably filled with a nutrient medium, the thickness of the carbon tubes being such that the bacteria can be immobilized in the membranes by filtration of a suspension of bacteria substantially along the outer surface of the tubes, and such that the nutrient medium can diffuse from the outer surface of the tubes to the inner surface of the tubes coated with the abovesaid membranes, the thickness of the carbon tubes being preferably of about 1 to about 3 mm and of the polyester tubes being preferably of about 100 to about 500$\mu$.

When xenobiotics must be degraded by specialized bacteria immobilized in the membranes of flat sheet reactor, tubular membrane reactor or continuous tubular membrane reactor, cell release needs to be reduced by a very low minimum).

When the tubular membrane is not supported by a tube, it is called a tubular membrane. For instance, the length is from about 30 to about 100 cm, the diameter is from about 5 to about 10 cm.

Figure 9:
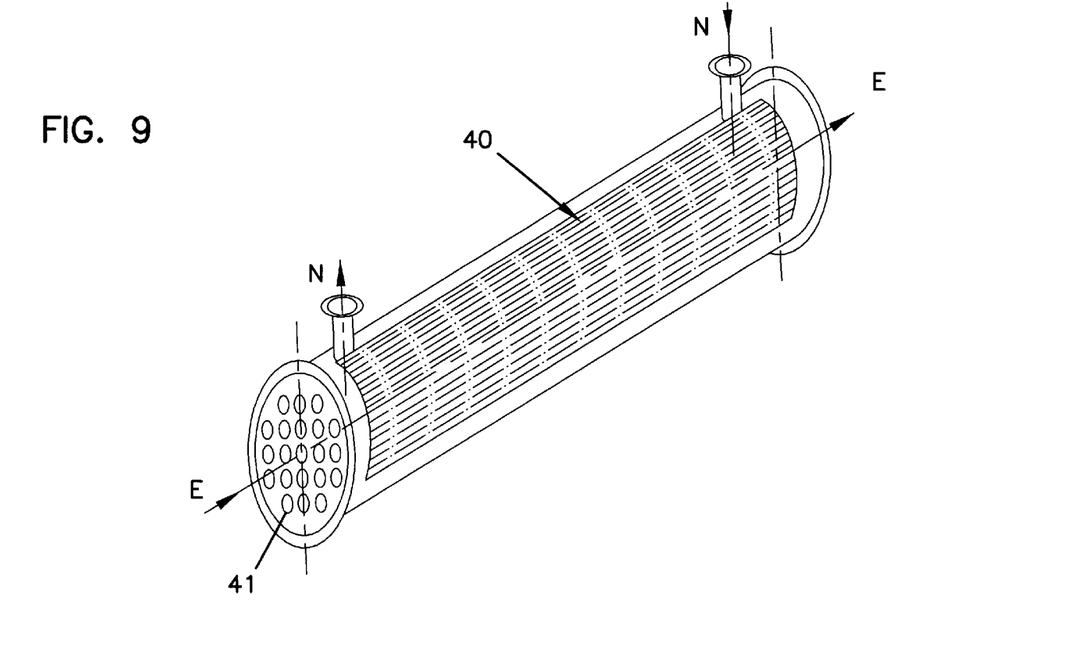
FIG. 9 represents a general view of a multiple tubular membrane reactor.

In this case, as shown in FIG. 9, another advantageous multipipe tubular membrane reactor can be realized. Such a reactor includes an outer tube 40 of the outer tubular housing G type (see FIG. 8) containing a lot of hollow fiber membranes 41. This embodiment allows the scaling up of the further described process.

According to the invention, wherein the pressure difference between each side of the membrane is about 0 and, when a solution is applied to one or both sides of the membrane, the pressure difference is lower than 20 mbar.

The pressure difference over the membrane will be defined as:

$$\Delta P = P2 - P1$$

in which P1=pressure in effluent

P2=pressure in nutrient.

When the reactor will be loaded (immobilization) with bacteria, $\Delta P$ will be slightly larger than zero in order to suck the bacteria into the membrane. During the growth of the bacteria in the membrane (colonization process) $\Delta P$ will be zero. For heavy metal removal, $\Delta P$ can be zero or slightly positive and for xenobiotic degradation, $\Delta P$ can be zero or slightly negative, in order to eliminate cell release in this case.

It is useful to bring oxygen to the membrane to promote the development of the above said biofilm.

Preferably, oxygen is brought to the membrane on the effluent side.

Preferably, there is no oxygen in the nutrient side.

The maximum amount of oxygen corresponds to saturation (i.e. about 10 mg of oxygen per liter).

The conditions in the reactor are such that there is growth of the microorganisms inside the membrane and not too much growth of the biofilm.

When the thickness of the biofilm is above about $100\mu$, bacteria can be released from the biofilm and this is preferably avoided, because it is a loss of bacteria [. . . ].

Moreover, when the thickness of the biofilm is above about $100\mu$, the bacteria which are close to the membrane are under anaerobic conditions and inefficient.

The preparation of the membranes with the immobilized microorganisms thereon and/or therein, can be carried out as follows:

the filtration of a suspension of microorganisms, containing an amount of microorganisms such that the membrane is not clogged and containing appropriate amounts of microorganisms, said suspension containing advantageously $10^8$ to $10^9$ microorganisms/ml, preferably $10^8$ microorganisms/ml, the filtration being carried out through the membrane, preferably in a tangential manner with respect to the surface of the membrane, in order to immobilize the microorganisms in and/or on the membrane.

The preparation of the membranes with the immobilized bacteria thereon and/or therein, can be carried out as follows:

the filtration of a suspension of bacteria, containing an amount of bacteria such that the membrane is not clogged and containing an appropriate amount of bacteria, said suspension containing advantageously $10^7$ to $10^8$ bacteria/ml, preferably $10^8$ bacteria/ml, the filtration being carried out through the membrane, preferably in a tangential manner with respect to the surface of the membrane, in order to immobilize the bacteria in and/or on the membrane.

If the filtration is tangential with respect to the membrane, the bacteria can settle in the pores or if not are released in the suspension, but clogging of the membrane is avoided.

If the filtration is perpendicular with respect to the membrane, bacteria settle upon each other and clogging appears.

The bacteria used are preferably constituted by an overnight culture ($10^9$ bacteria/ml), which is preferably about 10 times diluted, to avoid clogging.

If the suspension contains at least $10^9$ bacteria/ml, there is a risk of clogging of the membrane.

It is possible to use less than $10^7$ bacteria/ml, but under these conditions, it would be necessary to wait until enough bacteria have grown, otherwise the metal or xenobiotic elimination would last too long.

In the process for immobilizing the microorganisms on the membrane, it is advantageous to colonize the immobilized microorganisms, until the pores of the membrane are filled by the microorganisms on a thickness of about $100\mu$ to about $200\mu$, preferably in the whole thickness of the membrane, in the presence of an appropriate nutrient medium.

The colonization corresponds to the growth of the microorganisms inside the membrane, and also possibly on the membrane until a biofilm is obtained.

The colonization until the pores of the membrane are completely filled lasts advantageously 4 days.

The advantage of colonization is that there is a high concentration of bacteria and the treatment process is more efficient.

To prepare the membranes of the invention, the microorganisms are immobilized on the membranes after the preparation of the membranes, to be sure that the microorganisms are microorganisms trapped in the pores and not in the mass of the material of the membranes.

To prepare tubular membranes, resort may be had to the process described in European Patent Application No. 241995.

To prepare tubular membranes coated inside tubes or outside tubes, it is possible to resort to process known by the man skilled in the art, such as bringing a suspension of the components of the membrane to the shape of a hollow tube by means of a casting bob.

Said reactor can include anyone of the membranes of the invention above defined.

The bacteria, immobilized on a membrane, receive the nutrient by diffusion of said nutrient medium through the membrane.

The reactors of the invention can be used very well for the introduction of degradation of recalcitrant molecules by the principle of cometabolism. The advantage of this invention is that low amounts of substrate can be used for induction of cometabolism, compared to the stirred tank reactors where sometimes until 7 times higher substrate concentrations than the pollutant concentration are necessary.

The flat sheet reactor (FSR), continuous flat sheet reactor (CFSR), tubular membrane reactor (TMR) and continuous tubular membrane reactor (CTMR) can be used for the degradation of xenobiotic organic compounds, thanks to the immobilization of specialized xenobiotic organic compound degrading microorganisms. At the nutrient side, the bacteria can be provided with essential elements with or without some substrate in the use of very low pollutant concentrations, or in the case of cometabolism.

This system is then able to degrade the xenobiotics, such as chlorobiphenyl compounds, completely into water, $CO_2$ and NaCl (mineralization) if the right bacteria are used and if an appropriate substrate is used.

Examples of substrates are lactic acid, aromatic compounds, chloroaromatic compounds and polyaromatic compounds.

Additional Embodiments of the Invention

One embodiment includes a membrane having immobilized microorganisms therein or thereon. The membrane includes a porous material forming an open side and a skin side, and the porous material can contain an inorganic oxide and an organic polymer. The immobilized microorganisms are viable, and can be effective to precipitate at least one metal when in the presence of said metal. Alternatively, the microorganisms are effective to degrade one or more xenobiotic organic compounds when in the presence of said compound or compounds. The membrane can have pores constructed and arranged to immobilize the microorganisms. The pores can be arranged to communicate among themselves in such a manner that the microorganisms can colonize in the membrane. The microorganisms can colonize the membrane in such a way that release of microorganisms from the membrane can be less than about $10^4$ cells/ml/h. Advantageously, the release of microorganisms can be less than about $10^2$ microorganisms/ml/h.

A variety of types of microorganisms are compatible with the membranes of the invention. For example, in one embodiment the microorganisms are selected from the group consisting of fungi, yeast, algae, bacteria, and mixtures thereof. Advantageously, the microorganism is bacteria.

The pores in the membrane can be of various sizes and arrangements. In one embodiment, the pores can have an average size of about $1\mu$ to about $10\mu$ in the open side and less than about $1\mu$ in the skin side. Alternatively, the pores have an average size of about $1\mu$ to about $3\mu$ in the open side and less than about $1\mu$ in the skin side. One way to consider the size and arrangement of the pores is by the overall porosity of the membrane. Advantageously, the membrane has a porosity of about 50% to about 80%.

The thickness of the membrane can affect its performance as well. Advantageously, the thickness of the membrane is between about $50\mu$ and about $700\mu$.

The invention also includes a biofilm of microorganisms formed by a colonizing front of the microorganisms immobilized in the membrane. Typically, the size of the pores in the skin side of the membranes prevents the microorganisms from being released. The biofilm can form via cracks on the skin side of the membrane and from the microorganisms growing through and on the surface of the membrane. Advantageously, such a biofilm is formed on a membrane which the size of the membrane pores is less than about $1\mu$ at the skin side. In one embodiment of the biofilm, the microorganisms forming the biofilm are on the skin side of the membrane and the biofilm has a thickness of about 1μ to about 50μ.

A variety of types of microorganisms can form a biofilm and the biofilm can be formed in various different ways. In one embodiment, the microorganisms forming the biofilm are bacteria, and internal to the membrane the growing bacteria form the colonizing front from microcolonies around single dispersed bacteria in the membrane.

Microorganisms can also grow on or in the membrane in such a way that the microorganisms are immobilized and grow in the pores of the membrane. In this instance, a colonizing front of the growing microorganisms can form a biofilm of a thickness which varies from about 10μ to about 50μ.

The membrane of the invention can come in a variety of configurations. For example, the membrane can be flat or tubular, with or without a support. For example, the membrane can be selected from the group consisting of a flat membrane, a flat membrane without a support, a flat membrane with a support, a tubular membrane, a tubular membrane without a support, and a tubular membrane with a support. Advantageously, the membrane can be selected from the group consisting of a flat membrane without a support, a flat membrane with a support, a tubular membrane without a support, and a tubular membrane with a support. Advantageously, the membrane is tubular and has an inner diameter of greater than about 2 mm.

The various configurations of the membrane can accept different arrangements of the biofilm or microorganisms. For example, when the membrane is flat, a biofilm of microorganisms can be formed on the skin side of the membrane; and the skin side of the membrane can have a pore size lower than about 1μ and smaller than the pore size of the open side. In another embodiment, the membrane is tubular and a colonizing front of microorganisms is close to the skin side of the membrane. In this embodiment, the skin side of the membrane has pore size smaller than 1μ. The microorganism in this embodiment is bacteria.

When the membrane is in a tube, the membrane can coat the inner surface of the tube, which can be a carbon tube or a polyester tube. Typically, the larger size pores of the membrane are in contact with an inner surface of the tube and a biofilm formed by a colonizing front of the microorganisms is close to the skin side of the membrane.

Several types of organic and inorganic compounds are suitable components of the membrane of the invention. For example, the membrane can be made of polysulfone including an inorganic material. The membrane can include mixtures of organic and inorganic compounds. The membrane can be made of polysulfone including an inorganic material selected from the group consisting of $ZrO_2$, $Sb_2O_3$, $Al_2O_3$ and a combination of two of these inorganic materials.

The membrane can include $ZrO_2$ containing materials. The membrane can include $ZrO_2$ containing materials selected from the group consisting of polysulfone including polyvinylpyrrolidone (PVP), ZnO, and $CaCO_3$. The $ZrO_2$ containing materials can be polysulfone including polyvinylpyrrolidone (PVP) and/or an inorganic oxide selected from the group consisting of $ZrO_2$, $Sb_2O_3$, $Al_2O_3$, ZnO, and $CaCO_3$. The membrane can include $ZrO_2$, polysulfone, and materials selected from the group consisting of polyvinylpyrrolidone (PVP), ZnO, and $CaCO_3$. Alternatively, the membrane can be made of a porous material containing an inorganic oxide and an organic polymer. A typical organic polymer is polysulfone. Typical inorganic oxides can be selected from the group consisting of $ZrO_2$, $Sb_2O_3$, $Al_2O_3$, ZnO, and $CaCO_3$. The porous material containing an inorganic oxide and an organic polymer can be selected from the group consisting of polysulfone containing $ZrO_2$, $Sb_2O_3$, $Al_2O_3$, ZnO, or $CaCO_3$.

The porous material containing an inorganic oxide and an inorganic polymer can be $ZrO_2$ containing materials, or polysulfone comprising $ZrO_2$, $Sb_2O_3$, $Al_2O_3$, ZnO, or $CaCO_3$.

The membrane can be arranged so that a solution can be applied to one or both sides of the membrane. Typically, when a solution is applied to one or both sides of the membrane there is a pressure difference between each side of the membrane lower than about 20 mbar.

The membrane of the invention can be prepared by any of several processes. For example, a process for preparing a membrane having immobilized microorganisms therein or thereon can produce a membrane including a porous material. The porous material contains an inorganic oxide and an organic polymer. The process can produce a membrane in which the microorganisms are viable and effective to precipitate at least one metal when in the presence of said metal. Alternatively, the microorganisms can be effective to degrade one or more xenobiotic organic compounds when in the presence of said compound or compounds. The membrane made by the process has pores constructed and arranged to immobilize microorganisms. The pores communicate among themselves in such a manner that the microorganisms can colonize in the membrane. Also, release of microorganisms is less than about $10^4$ cells/ml/h. The process can include a step of filtering a suspension of microorganisms. This suspension can contain an amount of microorganisms such that the membrane is not clogged. The filtering through the membrane can be accomplished with tangential flow with respect to a surface of the membrane, to immobilize the microorganisms in or on the membrane. Advantageously, in this process the suspension contains about $10^8$ to $10^9$ microorganisms/ml. Also advantageously, in this process the suspension contains about $10^8$ microorganisms/ml.

In another embodiment, the process for preparing a membrane having immobilized microorganisms therein or thereon, can produce a membrane including a porous material. The porous material contains an inorganic oxide and an organic polymer. The process can produce a membrane in which the microorganisms can be viable and effective to precipitate at least one metal when in the presence of said metal. Alternatively, the microorganisms are effective to degrade one or more xenobiotic organic compounds when in the presence of said compound or compounds. The membrane made by the process has pores constructed and arranged to immobilize microorganisms. The pores communicate among themselves in such a manner that the microorganisms can colonize in the membrane. Release of microorganisms is less than about $10^5$ cells/ml/h. The process includes a step of filtering a suspension of bacteria. This suspension contains an amount of bacteria about $10^7$ to about $10^8$ bacteria/ml. Filtering is carried out through the membrane tangentially with respect to a surface of the membrane to immobilize the bacteria in or on the membrane.

The membranes of the invention can be used in a reactor of the invention. Such a reactor can contain a membrane having immobilized microorganisms therein or thereon. The membrane can include a porous material. The porous material can contain an inorganic oxide and an organic polymer. The microorganisms are viable and can be effective to precipitate at least one metal when in the presence of said metal. Alternatively, the microorganisms can be viable and effective to degrade one or more xenobiotic organic compounds when in the presence of said compound or compounds.

In this reactor, the membrane can have pores constructed and arranged to immobilize microorganisms. The pores can communicate among themselves in such a manner that the microorganisms can colonize in the membrane. Also, a release of microorganisms can be less than about $10^4$ cells/ml/h. This reactor also includes a support for the membrane. This reactor has first and second chambers, and each of said chambers has an inlet and an outlet. The first and second chambers are separated by a membrane containing pores of decreasing size from an open side to a skin side. The first chamber is in contact with the open side of the membrane. The second chamber is in contact with the skin side of the membrane.

The first chamber contains a nutrient medium to enable the life and growth of microorganisms and allow the microorganisms to form a biofilm of microorganisms on the skin side by bacterial transport through the membrane. The second chamber contains an effluent of metals or xenobiotic organic compounds to be treated by the biofilm. The biofilm is kept metabolically active by the nutrient, and the biofilm is effective remove metals or to degrade one or more xenobiotic organic compounds.

In one embodiment, the reactor of the invention includes a flat membrane. This membrane separates two chambers. Each chamber has an inlet and an outlet. One chamber has a nutrient medium and the other chamber contains a waste water effluent to be treated. The chamber containing the nutrient medium is in contact with one side of the membrane and the chamber containing the waste water effluent is in contact with the other side of the membrane.

Advantageously, in a reactor of the invention, the chamber containing the nutrient medium is in contact with the side of the membrane having larger pores and the chamber containing the effluent is in contact with the side of the membrane having smaller pores. Advantageously, in a reactor of the invention, the membrane has a biofilm of microorganisms located on the side of the membrane having smaller pores. Nutrients are provided to the biofilm in this embodiment by diffusion through the membrane from the nutrient side.

In another embodiment, the reactor of the invention includes a tubular housing, said tubular housing having hollow tubes of a porous material, such as carbon tubes or polyester tubes. The inner surface or the outer surface of the tubes is coated with a membrane, and the membrane is in contact with an effluent to be treated. The tubes have a thickness, the thickness being such that microorganisms can be immobilized in the membrane by filtration of a suspension of microorganisms substantially along an outer or inner surface of the tubes. The thickness of the tubes being such that a nutrient medium, which is either in the tubes or in an intertubular space, can diffuse from an outer or an inner surface of the tubes to the respective opposing surface of the tubes coated with the membrane.

The reactor of the invention can include a tubular housing, the tubular housing having hollow tubes including a porous material and said hollow tubes having an inner surface coated with a membrane having larger pores in contact with the inner surface of the tubes and smaller pores in contact with an effluent medium. The membrane includes an internal colonizing front close to a side having the smaller pores. The intertubular space is filled with a nutrient medium. The tubes have a thickness such that the microorganisms part is immobilized in the membrane by filtration of a suspension of microorganisms part is substantially along an outer surface of the tubes. The nutrient can diffuse from the outer surface of the tubes to the inner surface of the tubes which are coated with the membrane. The thickness of the tubes is about 1 mm to about 3 mm if the tubes are carbon, and from about $100\mu$ to about $500\mu$ if the tubes are polyester.

The reactor of the invention can include a recovery column integrated downstream of the cell. The recovery column can be constructed and arranged to recover metal, which has been precipitated together with microorganisms involved in said precipitation. The recovery column is filled with a material effective to adsorb metal. Advantageously, the material effective to adsorb metal is selected from the group consisting of glass beads, glass powder, glass wool, any form of silicate particles, sand particles and mixtures thereof.

The invention includes a process for precipitating metals or degrading xenobiotic organic compounds including administering a nutrient into one of the chambers of the reactor of the invention. The process also includes circulating effluents to be treated containing metals or one or more xenobiotic organic compounds in the effluent chamber of the reactor. The microorganisms in and on the membrane can induce precipitation and/or crystallization processes which result in the settling of metals. Alternatively, the microorganisms in and on the membrane can induce mineralization of one or more xenobiotic organic compounds, which results in degradation of said xenobiotic organic compounds into water, $CO_2$, and a mineral salt originating from the inorganic ions of said xenobiotic organic compounds and, possibly, from a substrate or cosubstrate that can be present. The process for precipitating metals or degrading xenobiotics can be carried out continuously or in batch.

The process can include forming a biofilm of these microorganisms on the membrane at the effluent chamber side, which puts the microorganisms into contact with the metals in solution. The process includes inducing precipitation and crystallization of the metals around the microorganisms. For example, contacting the biofilm with the metal in solution can induce precipitation or crystallization of the metal around the microorganisms.

The process for precipitating metals can include releasing microorganisms from the membrane into the effluent chamber, such that the microorganisms come into contact with the metals in solution. The process includes inducing precipitation and crystallization of the metals around the microorganisms. The crystallized metals can be recovered by a column such as a recovery column downstream of the reactor. For example, contacting the microorganisms with the metal in solution can induce precipitation or crystallization of the metals around the microorganisms. This allows recovering the precipitated or crystallized metals with a recovery column, such as a recovery column, downstream of the reactor.

The process for degrading one or more xenobiotic organic compounds can include a co-substrate for induction of cometabolism. This cosubstrate is used for mineralization of a xenobiotic compound by the microorganisms into water, $CO_2$, and either inorganic salts originating from inorganic ions of said xenobiotic organic compound and of said substrate. Alternatively, no substrate is used and any xenobiotic organic compound in the solutions to be treated are mineralized into water and CO2 by the microorganisms. Advantageously, in the process the microorganisms are in the presence of a cosubstrate for mineralizing a xenobiotic organic compound and the cosubstrate forms a mineral salt originating from the inorganic ions of the cosubstrate.

Advantageously, the process can include mineralizing a xenobiotic compound into water, carbon dioxide, and $Cl^-$ for chlorinated organic xenobiotic compounds to be treated. For example, in the process, a xenobiotic compound can be a chlorinated organic compound that is mineralized into water, carbon dioxide, and $Cl^-$.

Advantageously, process can include the co-substrate inducing the activity of an enzyme which degrades a xenobiotic substrate by the microorganisms. In some cases, the cosubstrate induces the activity of an enzyme by which the microorganisms degrade a xenobiotic organic compound.

The invention will be further described by reference to the following detailed examples.

EXAMPLES

Example 1

Removal of heavy metals:

The *Alcaligenes eutrophus* strain CH34 can be used for induction of precipitation and crystallization of heavy metals like cadmium, lead, zinc, nickel and copper.

At the nutrient side a carbon source (0.1% to 0.8% lactate), phosphate (from 0.1 to 1.0 mM) and ammonia (from 0.5 to 1 mM) are administered to keep the bacteria efficient for the precipitation process.

At the effluent side, water solutions containing cadmium (from 5 to 250 ppm), nickel (from 20 to 100 ppm), zinc (from 20 to 600 ppm), copper (from 20 to 60 ppm) and lead (from 5 to 250 ppm) can be circulated.

The bacteria in the membrane will induce precipitation and crystallization processes at the membrane which results in a settling of these metal precipitates on the membranes or on the walls of the recirculation tank. The metals can be removed from the walls by treatment with a 1N HCl solution.

More precisely, a membrane of a surface of 10 $CM^2$ is used. Said membrane is a polysulfonic membrane (18% of polysulfone) and contains 82% of $ZrO_2$.

It has a porosity of 70%, the size of the pores is from about 1 to about $2\mu$ and it has a thickness of $130\mu$ and one of its sides is a "skin side".

The immobilization of the bacteria is carried out with 100 ml of solution containing $10^8$ bacteria/ml (it is a dilution by 10 of an overnight culture) submitted to a tangential filtration which lasts 4 hours. The colonization is carried out for 4 days in the presence of a nutrient medium containing 0.2% of lactate, 1 mM of $Na_2HPO_4$, 2 mM of $NH_4OH$.

The pH of the effluent to be treated is of 7.8.

The flow rate of the nutrient medium is of 23 ml/min and the flow rate of the effluent medium to be treated is of 23 ml/min.

The treatment of the effluent lasts 36 hours.

With a solution containing 224 ppm of cadmium the yield of removal of cadmium is of about 98%.

Example 2

Degradation of PCB:

In the following example, the conditions used, except for the strain, are the same ones as the ones described in Example 1, with exceptions described below.

The pH of the effluent to be treated is between 6 and 8.

The *Alcaligenes eutrophus* strain A5 can be used for cometabolism of chlorinated biphenyl molecules.

At the nutrient side a cometabolizing carbon source (0.1–0.2%) is administered to keep the bacteria catabolizing (for instance biphenyl for the degradation of PCB). Also some phosphate (from 0.1 to 1.0 mM), and ammonia (from 0.5 to 5 mM) are fed to the immobilized bacteria. At the effluent side a water suspension containing some chlorinated biphenyls (from 0 to 2000 ppm) can be circulated. The biphenyls can bind easily to the hydrophobic membrane and there they will be catabolized by the immobilized bacteria.

In the case of A5 only mono-, di- and trichlorobiphenyls can be degraded.

Example 3

Synthesis of a melanine like polymer:

In the following example, the conditions are the same as the ones described in Example 1, except for the pH of the process solution which is from about 6 to about 8.

Some spontaneous mutants of *Alcaligenes eutrophus* CH34 (available to the man skilled in the art) can transform compounds like tyrosine and meta hydroxylated aromatics into black colored melanine like polymers.

At the nutrient side a mineral medium with gluconate (0.2%) as carbon source and 0.1% of tyrosine (the compound to be transformed) are administered (tyrosine can also be fed at the process solution side).

At the effluent side the end product polymer will appear and can be recovered without contamination of the original compound (e.g. tyrosine).

Example 4

Continuous tubular membrane reactor (CTMR)

FIG. 2 presents a Continuous Tubular Membrane Reactor (CTMR).

The system consists of an input (J), with metal contaminated effluent, an output (K), a nutrient vessel (A) and an effluent vessel (B) each foreseen with a filter (L). Further pump (I) pumps the effluent to vessel (B), from these it is pumped by pump (G) through the TMR (M) with immobilized bacteria in the membrane (E) into siphon (C) over a glass bead column (F) again into (B). Nutrient is pumped by pump (H) from (A) through the outer tubular space of (M) into siphon (D) back to (A).

With this system 1 liter effluent with 125 ppm Cd can be treated in minor than 20 hours to below 1 ppm Cd with a membrane surface of 16 $CM^2$. The same is true for the reduction of 70 ppm Zn to below 1 ppm Zn. The lactate consumption with this system is 0.3 g lactate/1 effluent.

At the membrane a minimum flow rate of between 100 and 200 ml/mn is necessary.

Example 5

The use of a TMR for degradation of organic compounds:

In a FSR, 500 ml of a solution containing 0.80% lactic acid was treated by immobilized *Alcaligenes eutrophus* CH34. The degradation of lactic acid was measured spectrophotometrically.

A degradation rate of 1 mg lactic acid/liter/hour. $cm^2$ membrane surface or 1 ppm lactic acid/hour/$cm^2$ membrane surface was obtained in a real crude first assay.

Higher rates can probably be obtained in a TMR and a CTMR.

The example shows the utility of the reactor system for degradation of small amounts (ppm to ppb level) of organic compounds in liquid effluents.

Example 6

Comparison between polysulfone and composite (polysulfone+$ZrO_2$) membrane:

Two FSR reactors were run with 1.0 mM Cd in the effluent stream. In one reactor, a composite Zirfon membrane (Zirfon=polysulfone+$ZrO_2$) was used and in the other a commercial polysulfone membrane.

The removal of Cd was measured in function of time. The following result was obtained: 112 ppm Cd was reduced to below 50 ppm Cd. Metal removal was faster with the Zirfon membrane than with the polysulfone membrane. Depending on the Zirfon membrane that is used, it can go up to 4 times faster.

The invention has been described with reference to various specific and preferred embodiments and techniques. However, it should be understood that many variations and modifications may be made while remaining within the spirit and scope of the invention. All publications and patent applications cited in this specification are indicative of the level of ordinary skill in the art to which this invention pertains.

We claim:

1. A method for precipitating a metal or degrading a xenobiotic organic compound, comprising the steps of:

providing a reactor having an effluent chamber, a nutrient chamber, and a porous membrane having an effluent chamber side and a nutrient chamber side, wherein said porous membrane is made of a porous material comprising an inorganic oxide and an organic polymer, said porous membrane having pores, a skin side on the effluent chamber side and an open side on the nutrient chamber side, a thickness of about 50 to about 700 microns and a porosity of about 50% to about 80%, said pores having an average size of greater than 2 micron to about 10 micron in the open side and less than 1 micron in the skin side, and said porous membrane separates the effluent chamber and the nutrient chamber such that leakage between a nutrient solution present in the nutrient chamber and an effluent solution present in the effluent chamber is prevented;

immobilizing a viable microorganism on the effluent chamber side of the porous membrane by forming a biofilm about 10 to 50 microns thick on the skin side of the membrane such that release of microorganisms from the membrane is less than about $10^4$ cells/ml/h;

adding a nutrient solution to the nutrient chamber, the nutrient solution providing nutrient to the microorganism by passing through the membrane from the open side to contact the microorganisms on the skin side, the concentration of nutrients in the nutrient chamber being kept sufficiently low such that the microorganism of the biofilm utilizes essentially all nutrients that pass through the membrane to prevent essentially any nutrient from entering the effluent solution;

adding an effluent solution comprising a metal, a xenobiotic compound or both to the effluent chamber; and contacting the microorganism with the effluent solution, wherein the contacting precipitates the metal or degrades the xenobiotic organic compound.

2. The method of claim 1, wherein forming the biofilm comprises growing microcolonies.

3. The method of claim 1, wherein immobilizing comprises filtering a suspension of microorganisms through the membrane, the suspension containing an amount of microorganisms such that the membrane is not clogged, the filtering through the membrane comprising tangential flow with respect to a surface of the membrane.

4. The method of claim 3, wherein the suspension contains about $10^8$ to about $10^9$ microorganisms/ml.

5. The method of claim 4, wherein the suspension contains about $10^8$ microorganisms/ml.

6. The method of claim 1, wherein adding the nutrient solution comprises circulating nutrient solution through the nutrient chamber.

7. The method of claim 1, wherein adding the effluent solution comprises circulating effluent solution through the effluent chamber.

8. The method of claim 1, wherein adding the nutrient solution comprises filling of the nutrient chamber with nutrient solution.

9. The method of claim 1, wherein adding the effluent solution comprises continuously filling of the effluent chamber with effluent solution.

10. The method of claim 1, wherein degrading the xenobiotic organic compound comprises converting the xenobiotic compound to products comprising water, $CO_2$, and a mineral salt originating from an inorganic ion of the xenobiotic organic compound.

11. The method of claim 10, wherein the xenobiotic compound is a chlorinated organic compound and is degraded into water, carbon dioxide, and $Cl^-$.

12. The method of claim 1, wherein the metal crystallizes.

13. The method of claim 1, wherein contacting the microorganism with the metal in the effluent solution induces precipitation or crystallization of the metal around the microorganism.

14. The method of claim 1, further comprising settling of the precipitated metal.

15. The method of claim 1, further comprising:

releasing microorganisms from the membrane into the effluent chamber;

inducing precipitation or crystallization of the metal around the microorganism; and recovering the precipitated or crystallized metals with a recovery column downstream of the reactor.

16. The method of claim 1, further comprising adding a compound having an inorganic moiety to either the effluent solution or the nutrient solution, wherein the compound is active in degrading the xenobiotic organic compound and forms a mineral salt originating from the inorganic moiety of the compound.

17. The method of claim 16, wherein the compound induces the activity of an enzyme by which the microorganisms degrade a xenobiotic organic compound.

18. The method of claim 1, wherein the microorganism is a fungus, an algae, a bacterium, or mixtures thereof.

19. The method of claim 18, wherein the microorganism is a yeast.

20. The method of claim 18, wherein the microorganism is bacteria.

21. The method of claim 1, wherein after adding the nutrient solution and the effluent solution there is a pressure difference between each side of the membrane lower than about 20 mbar.

22. The method of claim 1, wherein the porous membrane is a flat membrane or a tubular membrane.

23. The method of claim 22, wherein the porous membrane is a flat membrane without a support, a flat membrane with a support, a tubular membrane without a support, or a tubular membrane with a support.

24. The method of claim 22, wherein the porous membrane is tubular and wherein the tubular membrane has an inner diameter of greater than about 2 mm.

25. The method of claim 24, wherein the porous membrane coats the inner surface of a carbon tube or a polyester tube.

26. The method of claim 1, wherein the porous membrane is made of polysulfone comprising as an inorganic material selected from the group consisting of $ZrO_2$, $Sb_2O_3$, $Al_2O_3$ and a combination of two of these inorganic materials.

27. The method of claim 1, wherein the porous membrane comprises $ZrO_2$, polysulfone, and a material selected from the group consisting of polyvinylpyrrolidone (PVP), ZnO, and $CaCO_3$.

* * * * *